United States Patent [19]

Gurske

[11] 4,242,298

[45] Dec. 30, 1980

[54] POLYSACCHARIDE ESTER MEMBRANE CLEARING PROCESS

[75] Inventor: William A. Gurske, Placentia, Calif.

[73] Assignee: Beckman Instruments, Inc., Fullerton, Calif.

[21] Appl. No.: 55,585

[22] Filed: Jul. 9, 1979

[51] Int. Cl.$^3$ ............................................. B29B 11/22
[52] U.S. Cl. .................................. 264/233; 264/341; 264/343
[58] Field of Search ............... 264/233, 340, 341, 343; 252/364

[56] References Cited

U.S. PATENT DOCUMENTS

| | | | |
|---|---|---|---|
| 2,459,927 | 1/1949 | Dreyfus et al. | 264/343 |
| 3,424,640 | 1/1969 | Hines et al. | 264/343 |
| 3,592,672 | 7/1971 | Rowley et al. | 264/340 |
| 3,637,513 | 1/1972 | Schneider | 252/364 |
| 3,728,269 | 4/1973 | Stephenson et al. | 252/364 |

Primary Examiner—Hosea E. Taylor
Assistant Examiner—Amelia B. Yarbrough
Attorney, Agent, or Firm—R. J. Steinmeyer; R. R. Meads; Robert S. Frieman

[57] ABSTRACT

A method of clearing a polysaccharide ester membrane employing a clearing solvent comprising a first moiety selected from a group consisting of alcohols, ketones, ethers, esters, and mixtures thereof and a second moiety comprising a solvent selected from a group consisting of 2-ethoxyethanol, 2-ethoxyethyl acetate, methyl acetoacetate, ethyl acetoacetate, acetol, and mixtures thereof, the first moiety having a boiling point lower than the second moiety.

The solvents employed as the second moiety of the instant invention's clearing solvent are much less toxic than solvents employed as the second moiety of prior art clearing solvents.

16 Claims, No Drawings

POLYSACCHARIDE ESTER MEMBRANE CLEARING PROCESS

BACKGROUND OF THE INVENTION

1. Field of the Invention

The instant invention pertains to the treatment of polysaccharide ester films and more particularly to the production of clear polysaccharide ester films employing a solvent.

2. Description of the Prior Art

Cellulose acetate membranes are made up of a blend of cellulose acetate of varying degrees of acetate substitution. These membranes are produced in a way that will result in a highly porous matrix. With the proper blend of acetylated cellulose manufactured to the form of a highly porous matrix, one obtains a hydrophilic membrane capable of being employed for filtration or as a support media for an electrophoretic process.

To employ a cellulose acetate membrane in the electrophoretic process, one hydrates the membrane in an aqueous buffer and positions it in an electrophoretic cell. Once a sample has been applied to the surface of the membrane, a voltage potential is applied across the membrane to start the electrophoetic process. After a period of time, electrophoresis is terminated and the membrane is removed from the electrophoretic cell. The separated sample is detected by a chemical staining process to yield colored bands or spots on a white, opaque, cellulose acetate membrane background.

To quantitate the colored bands or spots, one must first transform the white opaque membrane into a clear, colorless film. This is known as the "clearing process" in electrophoretic methodology. The clearing process consists of the following steps. The membrane can be directly rinsed in a clearing solvent comprised of two fractions. Preferably, the membrane is first dehydrated in absolute alcohol and then rinsed in a clearing solvent comprised of two fractions. These rinsed membranes are placed on a suitable support, e.g., a glass plate, and dried, e.g., in an oven, at a suitable temperature, e.g., from about 70° to about 100° C. The dried cellulose acetate film is then removed from the support. This dried cellulose acetate membrane is now a clear, colorless cellulose acetate film still containing the colored bands or spots. These colored bands or spots can now be quantitated by scanning the clear cellulose acetate film with a densitometer or other suitable means. Therefore, the clearing process converts a non-transparent membrane into a transparent film to allow optical measurements to be performed upon substances located within the film.

The above described clearing process, as practiced in the prior art, employed as the clearing solvent one of the solutions set forth in Table I.

TABLE I

| First Component | Second Component |
|---|---|
| Alcohol* | glacial acetic acid. |
| Alcohol*: | cyclohexanone. |
| Water: | N,N-dimethyl formamide. |

*As used in this particular instance, the term "alcohol" encompasses methyl alcohol, ethyl alcohol, isopropyl alcohol, and mixtures thereof.

The solvents employed as the second component of the prior art solvents are relatively toxic as can be seen from the information set forth in Table II.

TABLE II[1]

| Solvent | $LD_{50}^{2}$, mg/kg | $LCL_o^3$ | TWA[4] |
|---|---|---|---|
| Cyclohexanone | 1620[5] | 2000 ppm/4H[6] | 50 ppm |
| N,N-dimethylformamide | 2800[5] | N/L[7] | 10 ppm |
| Acetic Acid | 3310[5,8] | 1600 ppm/4H[6] | 10 ppm |

[1]All data from Registry of Toxic Effects of Chemical Substances, Volume II, U.S. Department of HEW, Public Health Service, Center for Disease Control, National Institute for Occupational Safety and Health, Cincinnati, Ohio, 1977 Edition (September, 1977).
[2]For definition see ibid at page ix.
[3]For definition see ibid at page ix.
[4]For definition see ibid at page xi.
[5]Oral-rat
[6]Inhalation-Rat.
[7]N/L denotes not listed in Registry.
[8]Oral ingestion very serious; data listed for sodium acetate solution and not for acetic acid. See Patty, Industrial Hygiene and Toxicology, Vol II, 2nd Edition, Interscience Publishers, New York, N.Y. (1963).

Accordingly, for health and safety factors, it would be very desirable to be able to employ a less toxic solvent as the second component of a clearing solvent.

SUMMARY OF THE INVENTION

In accordance with the present invention there is provided several relatively less toxic solvents which can be employed as the second component of a clearing solvent.

In particular, the solvent employed as the second component of the present invention's clearing solvent is selected from a group consisting of 2-ethoxyethanol, 2-ethoxyethyl acetate, methyl acetoacetate, ethyl acetoacetate, acetol, and mixtures thereof.

These solvents are less toxic than the solvents employed as the second component of prior art clearing solutions as can be seen from the information set forth in Table III.

TABLE III[1]

| Solvent | $LD_{50}^{2}$, mg/kg | $LCL_o^3$ | TWA[4] |
|---|---|---|---|
| methyl acetoacetate | 3000[5] | N/L[6,7,8] | N/L |
| ethyl acetoacetate | 3980[5] | N/L[9,10] | N/L |
| acetol | 2200[5] | N/L[11] | N/L |
| 2-ethoxyethanol | 3000[5] | 4000 ppm/4H[12] | 200 ppm |
| 2-ethoxyethyl acetate | 5100[5] | 1500 ppm/8H[12] | 100 ppm |

[1]All data from Registry of Toxic Effects of Chemical Substances, Volume II, U.S. Department of HEW, Public Health Service, Center for Disease Control, National Institute for Occupational Safety and Health, Cincinnati, Ohio, 1977 Edition (September, 1977).
[2]For definition see ibid at page ix.
[3]For definition see ibid at page ix.
[4]For definition see ibid at page xi.
[5]Oral - rat.
[6]N/L denotes not listed in Registry.
[7]Exposure of rats to atmosphere calculated to contain 1370 ppm of methyl acetoacetate for a period of 6 hours produced no symptoms and the animal's growth, following exposure, was normal. Eastman Technical Data Sheet No. N-135 and Publication No. N-200, Eastman Chemical Products, Inc., Kingsport, Tenn.
[8]Exposure of rats to concentrated vapor of methyl acetoacetate for 8 hours was nonlethal. See Patty, Industrial Hygiene and Toxicology, 2nd Edition, Vol. II, Interscience Publishers, New York, N.Y. (1963).
[9]Exposure of rats to atmosphere calculated to contain 1129 ppm ethyl acetoacetate for a period of 6 hours produced no symptoms and the animal's growth, following exposure, was normal. Eastman Technical Data Sheet No. N-135 and Publication No. N-200, Eastman Chemical Products, Inc., Kingsport, Tenn.
[10]Exposure of rats to concentrated vapor of ethyl acetoacetate for 8 hours was nonlethal. See Patty, Industrial Hygiene and Toxicology, 2nd Edition, Vol. II, Interscience Publishers, New York, N.Y. (1963).
[11]Exposure of rats to known concentration of 2000 ppm of acetol for 8 hours was nonlethal. See Journal of Industrial Hygiene and Toxicology, 30(1):63–68 (1948).
[12]Inhilation - rat.

DESCRIPTION OF THE PREFERRED EMBODIMENTS

In the clearing solvent employed in the method of the instant invention it is preferred that the first component be selected from a group consisting of alcohols, ketones, ethers, esters, and mixtures thereof, wherein the boiling point of the first component is less than the boiling point of the second component. Preferably the first component has a boiling point of less than 120° C. at 760 mm Hg. Typical solvents having this criteria are methanol, ethanol, 1-propanol, 2-propanol, reagent alcohol, anhydrol (95 parts ethanol, 5 parts methanol, 10 parts 2-propanol, and 1 part methyl isobutyl ketone, and mixtures thereof. The composition of the first component must be such that it will not readily dissolve the polysaccharide ester membrane.

It is also preferred that the clearing solvent employed in the method of the instant invention comprise from about 40 to about 90 percent by volume of the first component and from about 10 to about 60 percent by volume of the second component. More preferably, the clearing solvent of the present invention comprises from about 50 to about 85 percent by volume of the first component and from about 15 to about 50 percent by volume of the second component.

To reduce the curling tendency of dried polysaccharide ester films, it is also preferred to add up to 10 percent by volume of a third fraction to the clearing solvents employed in the instant invention. This third fraction consists of a plasticizer selected from a group consisting of ether, ester, and carbohydrate derivatives, and mixtures thereof having a lower vapor pressure than the clearing solvent to which it is added. More preferably, up to 5 percent by volume of plasticizer is employed in the clearing solution of the instant invention. In addition the plasticizer should preferably have a boiling point greater than or equal to 200° C. at 760 mm Hg. Examples of plasticizers suitable for use in the clearing solvent employed in the method of the instant invention include glycerol triacetate, ethoxylated glucose derivatives, and trietylene glycol diacetate. The preferred plasticizer is glycerol triacetate.

Optimally, the clearing solvent of the instant invention comprises from about 48 to about 84% by volume of the first component, from about 14 to about 48% by volume of the second component, and from about 2 to about 4% by volume of the plasticizer.

Table IV lists several clearing solutions within the scope of this invention.

TABLE IV

| Clearing Solvent | Constituent | Percentage |
| --- | --- | --- |
| 1 | reagent alcohol | 50 |
|   | 2-ethoxyethanol | 50 |
| 2 | reagent alcohol | 70 |
|   | 2-ethoxyethyl acetate | 30 |
| 3 | reagent alcohol | 85 |
|   | methyl acetoacetate | 15 |
| 4 | reagent alcohol | 75 |
|   | ethyl acetoacetate | 25 |
| 5 | reagent alcohol | 75 |
|   | acetol | 25 |
| 6 | reagent alcohol | 80 |
|   | ethyl acetoacetate | 15 |
|   | methyl acetoacetate | 5 |
| 7 | anhydrol | 80 |
|   | ethyl acetoacetate | 15 |
|   | methyl acetoacetate | 5 |
| 8 | methanol | 45 |
|   | reagent alcohol | 40 |
|   | ethyl acetoacetate | 15 |

Any polysaccharide ester membrane can be employed in the clearing process of the instant invention. These polysaccharide ester membranes, as well as methods for their synthesis, are known to those skilled in the art. See, for example, Whistler et al., *Industrial and Engineering Chemistry*, 36(9): 796–803 (1944); Wolff et al., *Industrial and Engineering Chemistry*, 43(4): 911–914 (1951); Wolff et al., *Industrial and Engineering Chemistry*, 49(8): 1247–1248 (1957); Whistler et al., *Industrial and Engineering Chemistry*, 50(10): 1551 (1958); Carson et al., *J. Am. Chem. Soc.*, 68: 1015–1017 (1946); Smart et al., *Journal of Polymer Science*, 4: 87–90 (1949); Rao et al., *Proc. Ind. Acad. Sci.*, 424: 199–203 (1955); said publications being incorporated herein in toto by reference. Examples of polysaccharide ester membranes include, but are not limited to, cellulose acetate, tamarind acetate, amylose acetate, and guar acetate.

Due to its commercial availability, the preferred polysaccharide ester membrane employed in the process of the instant invention is a cellulose acetate membrane.

The following example is provided for the purpose of further illustration only and is not intended to be a limitation on the disclosed invention.

EXAMPLE 1

A cellulose acetate membrane, was electrophoresed, stained and destained for serum proteins, and then dehydrated in absolute alcohol for one minute. The membrane was rinsed for 40–60 seconds in a clearing solvent comprising 80% anhydrol, 15% ethyl acetoacetate, and 5% methyl acetoacetate. The membrane was placed upon a glass plate and the excess solvent removed with a squeegee. The membrane was then dried in an oven at about 75° C. for about 15 minutes. The cleared film was removed from the glass plate. The film had a highly satisfactory optically clear background. The film was then scanned with an optical densitometer at 520 nm corresponding to the absorprtion spectra of the dye employed in the experiments.

Example 1 demonstrates that the clearing solvents of the instant invention can be satisfactorily employed to clear polysaccharide ester membranes without the necessity of having to employ the relatively toxic second component solvents of the prior art.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A method of clearing a polysaccharide ester membrane comprising rinsing the membrane with a clearing solvent comprised of two components and drying the rinsed membrane, wherein the first component of said clearing solvent is selected from a group consisting of alcohols, ketones, ethers, esters, and mixtures and wherein said second component is selected from a group consisting of methyl acetoacetate, ethyl acetoacetate, acetol, 2-ethyoxyethanol, and 2-ethoxyethyl acetate, said first component having a boiling point less than said second component.

2. The method of claim 1 wherein said first component has a boiling point of less than 120° C. at 760 mm Hg.

3. The method of claim 2 wherein said clearing solvent further comprises a plasticizer selected from a group consisting of ether, ester, and carbohydrate derivatives having a lower vapor pressure than said clearing solvent to which it is to be added.

4. The method of claim 3 wherein said plasticizer has a boiling point greater than 200° C. at 760 mm Hg.

5. The method of claim 4 wherein said first component is selected from a group consisting of methanol, ethanol, 1-propanol, 2-propanol, reagent alcohol, anhydrol, and mixtures thereof.

6. The method of claim 5 wherein said clearing solvent comprises from about 40 to about 90% by volume of said first component from about 10 to about 60% by volume of said second component, and from about 0 to about 10% by volume of said plasticizer.

7. The method of claim 6 wherein said solvent comprises from about 50 to about 85% by volume of said first component, from about 15 to about 50% by volume of said second component and from about 0 to about 5% by volume of said plasticizer.

8. The method of claim 7 wherein said clearing solvent comprises from about 48 to about 84% by volume of said first component, from about 14 to about 48% by volume of said second component, and from about 2 to about 4% by volume of said plasticizer.

9. The method of claim 1 wherein said clearing solvent is selected from a group consisting of 50% reagent alcohol and 50% 2-ethoxyethanol; 70% reagent alcohol and 30% 2-ethoxyethyl acetate; 85% reagent alcohol and 15% methyl acetoacetate; 75% reagent alcohol and 25% ethyl acetoacetate; 75% reagent alcohol and 25% acetol; 80% reagent alcohol, 15% ethyl acetoacetate, and 5% methyl acetoacetate; 80% anhydrol, 15% ethyl acetoacetate, and 5% methyl acetoacetate; 45% methanol, 40% reagent alcohol, and 15% ethyl acetoacetate; said % being % by volume.

10. The method of claim 1 wherein said polysaccharide ester is selected from a group consisting of cellulose acetate, tamarind acetate, amylose acetate, and guar acetate.

11. The method of claim 1 wherein said polysaccharide is cellulose acetate.

12. The method of any one of claims 1–10 or 11 wherein prior to being rinsed in the clearing solvent the membrane is first dehydrated in absolute alcohol.

13. The method of any one of claims 3–7 or 8 wherein said plasticizer is selected from a group consisting of glycerol triacetate, ethoxylated glucose derivatives, and triethylene glycol diacetate.

14. The method of any one of claims 3–7 or 8 wherein said plasticizer is glycerol triacetate.

15. A clearing solvent for use in clearing a polysaccharide membrane comprising a first moiety selected from a group consisting of alcohols, ketones, ethers, esters, and mixtures thereof having a boiling point of less than 120° C. at 760 mm Hg and a second moiety selected from a group consisting of methyl acetoacetate, ethyl acetoacetate, acetol, 2-ethoxyethanol, and 2-ethoxyethyl acetate.

16. The clearing solvent of claim 15 further comprising a plasticizer selected from a group consisting of ether, ester, and carbohydrate derivatives having a lower vapor pressure than said clearing solvent to which it is to be added.

* * * * *